United States Patent
Hong et al.

(10) Patent No.: US 10,443,034 B2
(45) Date of Patent: Oct. 15, 2019

(54) STEM CELLS HAVING THIN MULTILAYER STRUCTURE

(71) Applicant: Chung-Ang University Industry-Academic Cooperation Foundation, Seoul (KR)

(72) Inventors: Jinkee Hong, Seoul (KR); Da Heui Choi, Chungcheongnam-do (KR); Eun Ah Lee, Seoul (KR)

(73) Assignee: Chung-Ang University Industry-Academic Cooperation Foundation, Seoul (KR)

( * ) Notice: Subject to any disclaimer, the term of this patent is extended or adjusted under 35 U.S.C. 154(b) by 246 days.

(21) Appl. No.: 15/234,284

(22) Filed: Aug. 11, 2016

(65) Prior Publication Data
US 2017/0044488 A1 Feb. 16, 2017

(30) Foreign Application Priority Data
Aug. 11, 2015 (KR) .................. 10-2015-0113013

(51) Int. Cl.
| | |
|---|---|
| *C12N 5/00* | (2006.01) |
| *A61K 9/50* | (2006.01) |
| *A61K 35/28* | (2015.01) |
| *C12N 5/0775* | (2010.01) |

(52) U.S. Cl.
CPC .......... *C12N 5/0006* (2013.01); *A61K 9/5031* (2013.01); *A61K 9/5052* (2013.01); *A61K 9/5073* (2013.01); *A61K 35/28* (2013.01); *C12N 5/0663* (2013.01); *C12N 2533/32* (2013.01); *C12N 2533/50* (2013.01); *C12N 2533/80* (2013.01)

(58) Field of Classification Search
CPC .......... C12N 5/0006; C12N 2533/32; C12N 2533/50; C12N 2533/80; A61K 9/5031; A61K 9/5052; A61K 9/5073
See application file for complete search history.

(56) References Cited

U.S. PATENT DOCUMENTS

2008/0248108 A1* 10/2008 Krotz .................. A61K 9/1652
424/463

FOREIGN PATENT DOCUMENTS

WO WO2010028087 A2 3/2010

OTHER PUBLICATIONS

Arginylglycylaspartic acid. Datasheet [online]. Wikipedia, 2018 [retrieved Mar. 30, 2018]. Retrieved from the Internet: <URL: https://en.wikipedia.org/wiki/Arginylglycylaspartic_acid>.*

(Continued)

*Primary Examiner* — Kara D Johnson
(74) *Attorney, Agent, or Firm* — Masuvalley & Partners

(57) ABSTRACT

Disclosed are stem cells having a thin multilayer structure, a method of preparing the same, and use thereof for cytotherapy. In accordance with the present invention, stem cells with a thin multilayer structure having improved stability and controlled multifunctionality are provided. A method of preparing the stem cells having the thin multilayer structure according to the present invention is very simple, and thus, the stem cells having the thin multilayer structure can be produced at low cost and high efficiency. Therefore, the stem cells having the thin multilayer structure prepared according to the present invention are very useful as a stem cell therapy agent for treating various diseases.

3 Claims, 7 Drawing Sheets

(56) References Cited

OTHER PUBLICATIONS

Choi, Daheui et al., Nano-Sized multilayer films onto stem cells for enhanced cell viability, 2014 Fall Meeting of The Korea Society for Biomaterials, Nov. 6, 2014, pp. 1-2.
Choi, Daheui et al., Functional nano-films on stem cells surface for enhanced stability from external stress, TERMIS-AP 2014, Tissue Engineering and Regenerative Medicine International Society Asia-Pacific Annual Coference 2014, Sep. 24, 2014, pp. 1-3.
Lee, Juno et al., Cytoprotective Silica Coating of Individual Mammalian Cells through Bioinspired Silification, Angewandte Communications, Wiley Online Library, Jun. 4, 2014, pp. 8056-8059.
Matsuzawa, Atushi et al., Effectiveness of Nanometer-Sized Extracellular Matrix Layer-by-Layer Assembled Films for a Cell Membrane Coating Protecting Cells from Physical Stress, American Chemical Society Publications—Langmuir, Oct. 23, 2012, vol. 29, pp. 7362-7368.
Tyndall, Alan et al., Mesenchymal Stem Cells Combat Sepsis, Nature Medicine, Jan. 2009, vol. 15—No. 1, pp. 18-19.

* cited by examiner

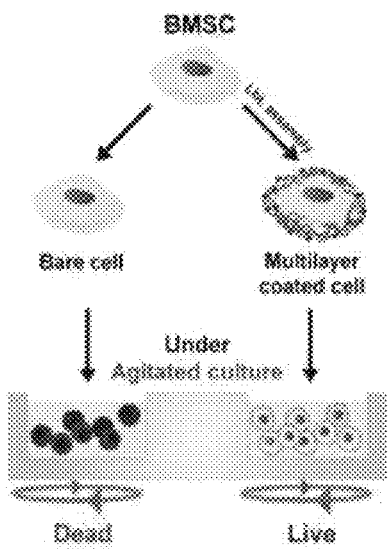
FIG. 1A  FIG. 1B
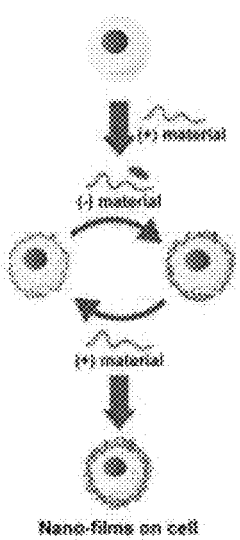
FIG. 1C
FIG. 2A
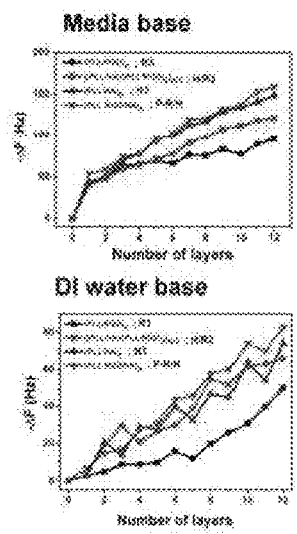
FIG. 2C
FIG. 2B
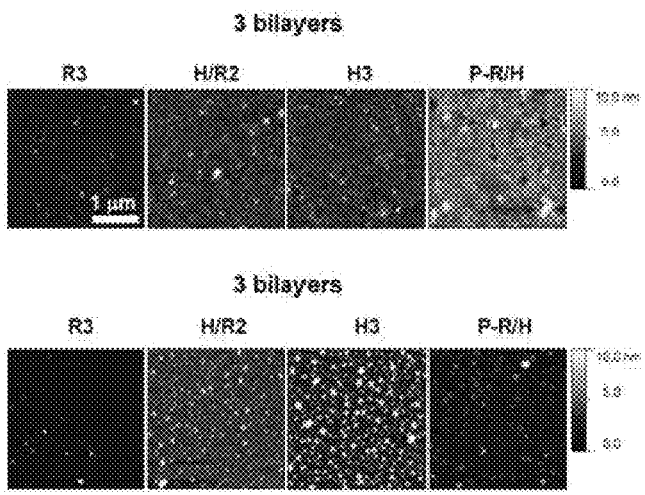
FIG. 2D

FIG. 9A
FIG. 9C
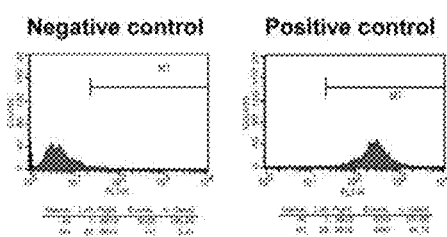
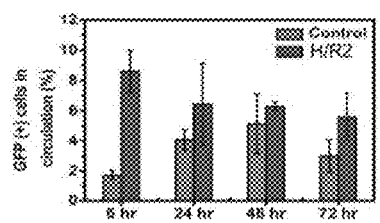
FIG. 9 B
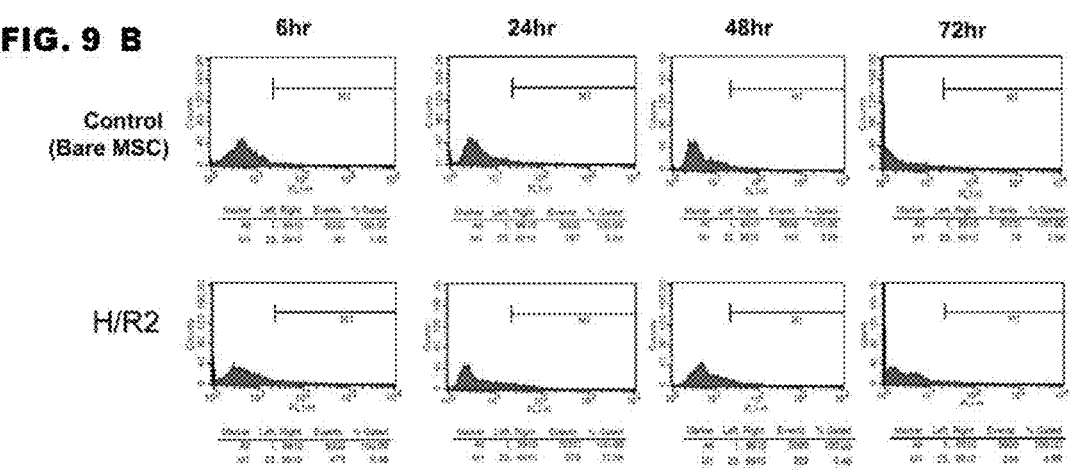

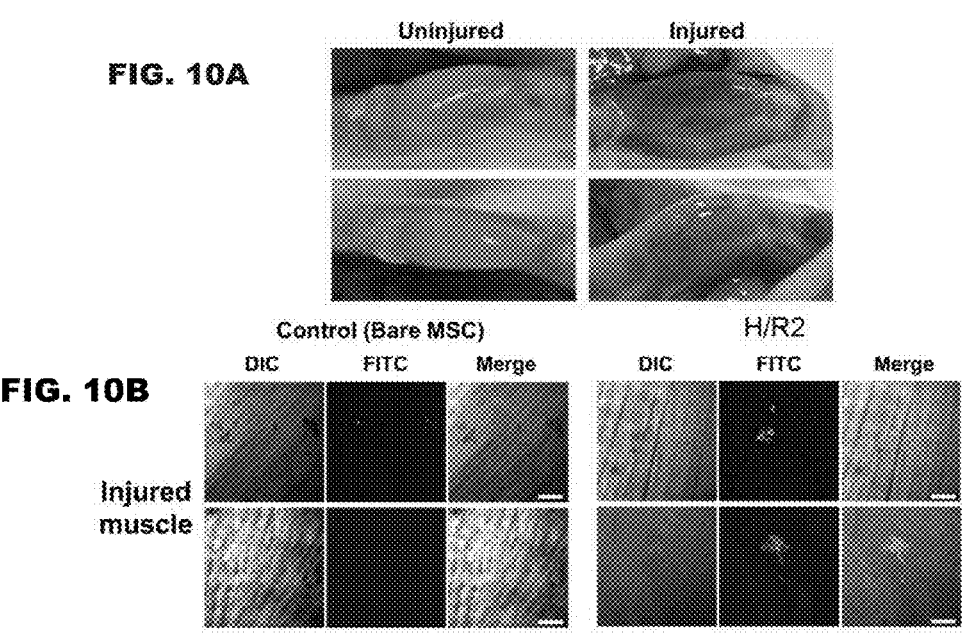

STEM CELLS HAVING THIN MULTILAYER STRUCTURE

RELATED APPLICATIONS

This application claims priority to and the benefit of Korean Patent Application No. 10-2015-0113013, filed on Aug. 11, 2015, the disclosure of which is incorporated herein by reference in its entirety.

BACKGROUND OF THE INVENTION

1. Field of the Invention

The present invention relates to stem cells having a thin multilayer structure, a method of preparing the same, and use thereof for cytotherapy.

2. Discussion of Related Art

Mesenchymal stem cells have the ability to differentiate into various tissue cells, thus attracting attention as a therapeutic material for treatment of immune-related diseases or tissue regeneration. Accordingly, a variety of research into mesenchymal stem cells is actively underway. However, despite such usability, the utilization of mesenchymal stem cells as a therapeutic agent is known to be limited due to intrinsic vulnerability thereof. As an example, a method of simply injecting a single stem cell into the blood is mainly used in treatment of immune-related diseases (A. Tyndall and V. Pistoia, Nature Medicine, 2009, 15, 18). However, upon such single cell injection, the stability of the injected single cell is decreased and it is difficult to deliver the single cell to a target tissue or organ due to various physical, chemical stresses in the blood having high pressure and speed. In addition, when stem cells differentiate into various cells and tissues, the stem cells should be treated in a specific differentiation medium for a long time to induce differentiation thereof, which is an inconvenient process.

To overcome such disadvantages, research into improving the stability and functions of cells by modifying surfaces thereof has been reported. The Ali Khademhosseini group in the U.S. developed a cell culture platform which is stable relative to various chemical stimuli by attaching mouse cardiocytes to gelatin hydrogel and then covering surfaces of the cells with silica hydrogel in a sol-gel manner in order to stably and easily culture cells (C. Cha et al., Biomacromolecules, 2014, 15, 283). In addition, the Akashi group in Japan produced a thin multilayer film using fibronectin, gelatin, which is ECM components, as building materials of an actual ECM in order to stably maintain cells under external physical stress (strong centrifugal force) (A. Matsuzawa et al., Langmuir, 2014, 29, 7362). Further, the Choi group developed stable cells with respect to external enzymes, such as trypsin, by silica-coating HeLa cells (J. Lee et al., Angewante Chemie International Edition, 2014, 53, 8056).

However, conventional technologies relate to cells having relatively high survivability, except for normal stem cells, whereby, when the technologies are applied to stem cells, survivability or functionality thereof may be reduced. In addition, since most conventional cell coating technologies under investigation relate to a technology of coating silica with low penetrability and metal-based materials, various cell-cell interactions are spontaneously deteriorated. Accordingly, application of the technologies to stem cells is not appropriate. In addition, since conventional technologies are performed in an environment different from a real cell culture environment, they are not suitable for stem cell culture.

Therefore, there is a need for a new method of improving the stability of stem cells in an environment similar to a real cell culture environment.

SUMMARY OF THE INVENTION

Therefore, the present invention has been made in view of the above problems, and it is an object of the present invention to provide stem cells with a thin multilayer structure having improved stability in a practical cell culture environment and controlled multifunctionality, a method of preparing the same, and use thereof as a cell therapy agent.

In accordance with the present invention, the above and other objects can be accomplished by the provision of a stem cell having a thin multilayer structure, wherein the stem cell includes a cationic material layer formed on the stem cell; and an anionic material layer formed on the cationic material layer, wherein at least one of the cationic and anionic material layers is composed of a low molecular weight substance having a weight-average molecular weight of 1000 or less.

In accordance with another aspect of the present invention, there is provided a method of preparing a stem cell having a thin multilayer structure, the method including:

a step of laminating a cationic material on a stem cell in a layer-by-layer fashion to form the cationic material layer on the stem cell;

a step of laminating an anionic material on the cationic material layer in a layer-by-layer fashion to form the anionic material layer on the cationic material layer; and a step of alternately forming the cationic material layer and the anionic material layer one or more times, wherein at least one of the cationic and anionic material layers is composed of a low molecular weight substance having a weight-average molecular weight of 1000.

In accordance with still another aspect of the present invention, there is provided a therapeutic stem cell composition including the stem cell having the thin multilayer structure.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1A is a schematic diagram illustrating an agitation culture process of stem cells;

FIG. 1B is a schematic diagram illustrating a process of forming a thin multilayer film on a surface of a mesenchymal stem cell (MSC);

FIG. 1C illustrates components of a thin multilayer film;

FIGS. 2A through 2D illustrate characteristic analysis results of thin multilayer films in accordance with solvent type (standard media, DI water);

FIGS. 9A through 9C illustrate effects of nanofilms on in vivo stem cell survival after systemic transplantation. GFP (+) MSCs with or without nanofilms were injected into immunocompromised mice through tail veins and whole blood was withdrawn at the indicated time interval to examine the proportion of GFP (+) MSCs in circulation (n=4). Mononuclear cells isolated from non-injected mice and GFP (+) MSCs (b) served as negative and positive controls (a), respectively; and FIGS. 10A and 10B illustrate stem cell recruitment in a muscle injury model. FIG. 10A is an image of injured muscle on single side of femur after injection of GFP (+) MSCs with or without a nanofilm. FIG. 10B is a two-photon microscopy images of recruited GFP (+) MSCs (FITC) in injured muscles. The muscles were sliced to a thickness of 1 mm to detect GFP (+) cells 2 days after cell injection. GPF (+) cell clusters were detected in control mice (n=5). The white bar indicates 100 mm.

DETAILED DESCRIPTION OF EXEMPLARY EMBODIMENTS

Figure 3:
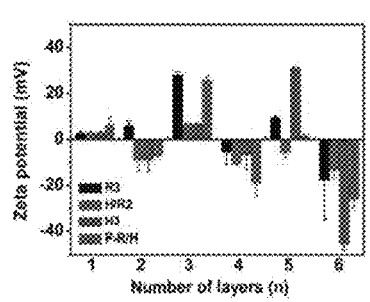
FIGS. 3A and 3B illustrate zeta potential change according to introduction of a thin multilayer film and SEM image analysis results after thin multilayer film introduction.
Figure 3:
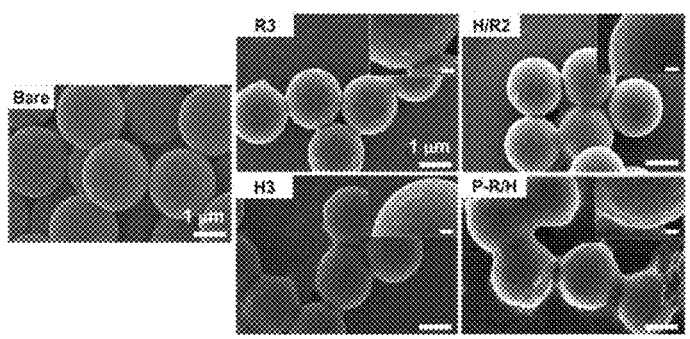

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present invention provides stem cells having a thin multilayer structure, the stem cells including a cationic material layer formed on the stem cells; and an anionic material layer formed on the cationic material layer.

In the present invention, the expression "formed on" refers to not only the case in which corresponding components are stacked while directly contacting each other, but also the case in which another component is further formed between corresponding components. For example, the expression "formed on" refers to not only the case in which a second component is formed on a surface of a first component while directly contacting the first component, but also the case in which a third component is further formed between the first and second components.

In an embodiment, at least one of the cationic and anionic material layers may be composed of a low molecular weight substance having a weight-average molecular weight of 1000 or less. In accordance with the present invention, the stability and survival rate of stem cells may be improved by laminating a low molecular weight substance itself on a surface of each of the stem cells.

In an embodiment, the low molecular weight substance is not specifically limited so long as it has a weight-average molecular weight of 1000 or less and may maintain or improve the stability and survival rate of stem cells. For example, the low molecular weight substance may be an RGD peptide. The stability and survival rate of stem cells may be improved by laminating the RGD peptide on each of the stem cells.

In an embodiment, stem cells may be, without being limited to, bone marrow-derived stem cells.

In an embodiment, the cationic material may be one or more selected from the group consisting of polyhistidine, polyarginine, chitosan, poly(beta-amino ester), poly(ethylene imide) and poly-L-lysine, the anionic material may be one or more selected from the group consisting of poly(glutamic acid), poly(aspartic acid), heparin sulfate, hyaluronic acid, chondroitin sulfate, alginate, keratan sulfate, and dextran sulfate, and the low molecular weight substance may be one or more selected from the group consisting of dexamethasone, methotrexate, doxorubicin, alkaloids, glycosides, polyketide, tannic acid, and an RGD peptide.

In an embodiment, the cationic or anionic material may be represented by Formula 1 below:

$$(\text{poly-M})_k \quad\quad\quad [\text{Formula 1}]$$

wherein M represents lysine, histidine, arginine, glutamic acid, or aspartic acid, and k represents 2 to 50.

In an embodiment, hyaluronic acid may have a weight-average molecular weight of 500 kDa to 1200 kDa.

In an embodiment, the cationic material may be poly-L-lysine or poly-L-lysine conjugated with an RGD peptide, the anionic material may be hyaluronic acid or an RGD peptide, and at least one of the cationic and anionic material layers may include an RGD peptide.

In an embodiment, the cationic material layer may be alternately laminated with the anionic material layer one or more times.

The cationic material constituting the thin multilayer film of the stem cell having a thin multilayer structure according to an embodiment of the present invention may be poly-L-lysine (PLL) or poly-L-lysine conjugated with an RGD peptide (Arg-Gly-AspRGD), and the anionic material constituting the same may be hyaluronic acid (HA) or an RGD peptide. In particular, the thin multilayer film may have a structure wherein a PLL layer, as the cationic material layer, and an RGD layer, as an anionic material layer, are alternately laminated (PLL/RGD). In addition, the PLL/RGD layers may be laminated one to five times.

The thin multilayer film according to another embodiment of the present invention may have a structure wherein a first layer including the PLL layer, as a cationic material layer, and a HA layer, as an anionic material layer, and a second layer including a PLL layer, as a cationic material layer, and an RGD layer, as an anionic material layer are alternately laminated. Here, a lamination ratio of the first layer and the second layer may be 1:1 to 1:3, or 1:2.

The thin multilayer film according to another embodiment of the present invention, the cationic material layer may have a structure wherein the PLL layer conjugated with an RGD peptide and the HA layer are alternately laminated. Here, the PLL layer and the HA layer may be laminated one or five times.

The thin multilayer film according to an embodiment of the present invention may include, other than the cationic and anionic material layers, an additional material. For example, various factors facilitating proliferation and differentiation of stem cells (e.g., TGF-beta) or growth factors facilitating differentiation into osteoblasts (e.g., BMP-2) may be further included. When the growth factors are additionally included, the growth factors have a specific charge density at specific pH and thus may bind with a specific polymer by electrostatic attraction, thereby forming a thin layer with the polymer.

The present invention also provides a method of preparing the stem cells having a thin multilayer structure, the method including:

a step of laminating a cationic material on stem cells in a layer-by-layer fashion to form the cationic material layer;

a step of laminating an anionic material on the cationic material layer in a layer-by-layer fashion to form the anionic material layer; and a step of alternately forming the cationic material layer and the anionic material layer one or more times.

All of the aforementioned content with respect to the stem cells having a thin multilayer structure may be directly applied or applied with necessary changes to the method of preparing the stem cells having a thin multilayer structure.

In particular, a cationic material layer may be formed on stem cells by adding a positively charged solution including the cationic material dissolved therein and an anionic material layer may be formed on the cationic material layer by adding a negatively charged solution including an anionic material dissolved therein to the cationic material layer. This process may be repeated one or more times to form a thin film having a desired number of layers.

In an embodiment, at least one of the cationic and anionic material layers may be composed of a low molecular weight substance having a weight-average molecular weight of 1000 or less.

The present invention is characterized by using a low molecular weight RGD peptide as one ingredient of the thin film. Surplus ions in low molecular weight substances having two carboxyl groups therein like the RGD peptide are not sufficient, and thus, the molecules have been considered not to be suitable for lamination in a layer-by-layer fashion. Accordingly, the low molecular weight substances have been used only in a conjugated form with a polymer material. In the case of conventional layer-by-layer deposition methods, only a material such as a polymer, wherein the electric charge in one molecule is sufficient and by which a following layer is sufficiently formed, is used to prepare thin multilayer films. However, although the RGD peptide of the present invention is a low molecular weight substance having a weight-average molecular weight of 100 to 500 and thus the number of anions present in one molecule is small, the RGD peptide reacts with a cationic material in a ratio of 1 to greater than 1, not in a ratio of 1 to 1, whereupon binding with the cationic material, a thin multilayer film may be prepared. In particular, since the RGD peptide binds to the cationic material in a manner in which multiple cations of the cationic material share one anion, a thin film may be sufficiently formed even in the case of a low molecular weight substance. In the case of materials formed by ionic bonding, ions are not bonded to each other in a ratio of 1 to 1, and one ion is shared by counterions present near the ion. Based on this principle, a principle of preparing a thin film may be indirectly described. In addition, in the case of the RGD peptide, various functional groups (NH2, NH, and C=O bonds) that may be bonded through hydrogen bonding are present and, whereupon preparation of a thin film, the RGD peptide may be bonded by hydrogen bonding as well as ionic bonding. Accordingly, the RGD peptide allows successful thin multilayer film preparation despite a low molecular weight thereof.

In an embodiment, the cationic material may be poly-L-lysine or poly-L-lysine conjugated with an RGD peptide, the anionic material may be hyaluronic acid or an RGD peptide, and at least one of the cationic and anionic material layers may include an RGD peptide.

The present invention also provides a therapeutic stem cell composition including stem cells having a thin multilayer structure. Since the stem cells having a thin multilayer structure prepared according to the present invention have improved stability and the stem cell potency may be controlled depending upon ingredients of the thin film and a lamination frequency, the therapeutic stem cell composition may be utilized as a therapeutic agent for treatment of various diseases (immune-related diseases, wound healing, tissue regeneration, etc.).

The stem cells having a thin multilayer structure may be included in a content of 0.01% to 100%, preferably 1% to 50%, based on a total weight of the composition of the present invention. The content may be suitably controlled depending upon the contents of other ingredients in a formulation thereof or the composition. However, when the content of the stem cells having a thin multilayer structure in the composition is less than 0.01%, it may be difficult to anticipate substantial effects. When the content is greater than 50%, economic efficiency may be low with respect to anticipated effects. Therefore, the content is preferably 0.01% to 50% based on a total weight of the composition.

In an embodiment of the present invention, the composition of the present invention may further include at least one pharmaceutically acceptable carrier. The pharmaceutically acceptable carrier may be, without being limited to, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, mineral oil, or the like commonly used for formulation. The pharmaceutical composition of the present invention may further include, other than the carrier, a lubricant, a wetting agent, a sweetener, a flavoring agent, an emulsifier, a suspension, a preservative, etc.

In addition, in another aspect of the present invention, the present invention relates to a method of treating a wound, the method applying a therapeutically effective amount of the aforementioned stem cells having a thin multilayer structure to a wound area in a composition form.

The "therapeutically effective amount" of the cells is an amount sufficient to eliminate or alleviate physical symptoms in patients. The therapeutically effective amount of the cells depends upon the need, age, physiological state, and heath state of a patient, therapeutic effect, the size and area of a target tissue to be treated, a lesion state, and a selected delivery path.

A suitable number of cells administered to accomplish therapeutic effect may be suitably adjusted depending upon patients based on common knowledge among those skilled in the art. For example, the cells may be administered in a number of about 1,000 to 10,000,000, or more. However, since the cells may be changed into cancer cells upon administration of a high number of the cells, the number of the cells is preferably about 100,000 to 4,000,000.

However, an administration amount of the cells is not limited to the above range, and may be suitably determined by a physician's final judgment in consideration of formulation type, administration path, the age or weight of patients, symptoms of patients, etc.

The composition of the present invention may be orally or parenterally administered. Upon parenteral administration, the composition may be administered by spreading, intravenous injection, subcutaneous injection, intramuscular injection, intraperitoneal injection, percutaneous administration, etc. For example, when the pharmaceutical composition of the present invention is used for wound healing, the composition is preferably administered by topically spreading the same on a skin having a wound.

Now, the present invention will be described in more detail with reference to the following preferred examples.

These examples are provided for illustrative purposes only and should not be construed as limiting the scope and spirit of the present invention.

EXAMPLE

Preparation Example 1

Synthesis of poly-L-lysine Conjugated with RGD Peptide 1 mg of an RGD peptide, 0.624 mg of N-(3-Dimethylaminopropyl)-N'-ethylcarbodiimide hydrochloride (EDC), and 0.353 mg of N-hydroxysulfosuccinimide sodium salt (sulfo-NHS) were added to a 0.1 M (N-morpholino)ethanesulfonic acid (MES) solution, followed by strong stirring for about 30 minutes. To a resultant mixture, 32.6 mg of a PLL solution dissolved in a 0.1 M MES solution was slowly added. Stirring was strongly performed for about 12 hours such that synthesis was induced. Only pure PLL-RGD was isolated through a dialysis membrane (MWCO 3500), followed by lyophilization. As a result, a target material was obtained in a powder form.

Preparation Example 2

Preparation of Polystyrene (PS) Microparticles Having Thin Multilayer Structure PS particles (Sigma-Aldrich) were dispersed in distilled water and centrifuged for five minutes, thereby obtaining purified PS particles. Since PS microparticles inherently have a negative charge, 0.5 ml of PLL (1 mg/ml), as a material having a positive charge, was added to the PS particles, followed by rapid stirring for five minutes and ultrasonicating to induce attachment of PLL to the surfaces of the PS particles by electrostatic attraction. Subsequently, centrifugation was rapidly performed at 12,000 rpm for five minutes, thereby extracting PLL-adsorbed PS particles. 1 ml of distilled water was added to the PS particles, followed by stirring for one minute and ultrasonicating to remove the remainder of PLL. This process was repeated twice. PS particles having a thin multilayer structure were prepared using 1 mg/ml hyaluronic acid (HA) as a material having a negative charge, and 0.25 mg/ml of the RGD peptide as previous PLL layer. The configuration of the thin multilayer film is illustrated in FIG. 10. Solvents for all of the materials were standard media purchased from Gibco (composition of the standard media: 5 ml of dexamethasone (Dex, 10-8 M), 5 ml of penicillin, 5 ml of ascorbic acid (10-4M), 5 ml of 200 mM L-glutamine, 100 ml of FBS, and 380 ml of MEM-alpha).

Preparation Example 3

Preparation of Thin Multilayer Film on Various Substrates

To perform a quartz crystal microbalance (QCM) experiment, a thin multilayer film was prepared on an Au—Cr electrode, and a thin multilayer film was prepared on a silicone wafer to perform AFM analysis. To wash the electrode and induce a negative charge, a piranha solution including sulfuric acid and hydrogen peroxide mixed in a ratio of 3:1 (H. Lu et al., Journal of Material Chemistry, 2011, 21, 10878-10882) was prepared and treated on the Au—Cr electrode for about five minutes. The silicone wafer was induced to a negative charge using oxygen plasma before using.

The negative charge-induced substrate was immersed in a PLL solution for about 10 minutes, followed by washing for one minute twice. Subsequently, the substrate was immersed in positively and negatively charged solutions in the same manner as in Preparation Example 2 to form a thin multilayer film on the substrate. The concentration of each of HA, PLL and RGD peptide-PLL was 1 mg/ml, and the concentration of the RGD peptide was 0.25 mg/ml. A solvent for all of the materials was a standard media (the composition of the standard media: 5 ml of dexamethasone (Dex, 10-8 M), 5 ml of penicillin, 5 ml of ascorbic acid (10-4M), 5 ml of 200 mM L-glutamine, 100 ml of FBS, and 380 ml of MEM-alpha). As a control, a thin multilayer film was used using deionized water (DI water) with the same pH as a solvent. Components of the thin multilayer film are illustrated in FIG. 1C.

Preparation Example 4

Preparation of Mesenchymal Stem Cells Having Thin Multilayer Structure

Cell Culture

Human bone marrow stromal cells (BMSCs) were provided from Kangnam St. Peter's hospital. The BMSCs were obtained by aspirating the bone mass and bone marrow from a patient. The obtained cells were centrifuged at 2,200 rpm for 20 minutes, thereby preparing a pellet. The cells were washed with PBS and then suspended in the standard media. 5×106 suspended cells were seeded in a 100 mm petri dish. The seeded cells were cultured in a 5% CO2 incubator at 37° C. Upon re-culturing of the cells, a solution prepared by dissolving 0.25% trypsin and 1 mM EDTA in Hank's Balanced Salt Solution (HBSS) was used.

Preparation of Mesenchymal Stem Cells Having Thin Multilayer Structure

Mesenchymal stem cells cultured in a 37° C. incubator were trypsinized to be individually separated. Subsequently, individually separated cells were obtained by centrifuging at 1,500 rpm for five minutes. The surfaces of the individually separated stem cells had a negative charge, and thus, a thin multilayer film was introduced to a surface of each of the stem cells in a manner similar to that of Preparation Example 2. In particular, 0.5 ml of a positively charged solution was added to the stem cells and pipetting was performed for about one minute by means of a 1 ml pipet. Subsequently, centrifugation was carried out at 1,500 rpm for five minutes to extract only cells. To remove remaining materials, 1 ml of α-MEM was added and then pipetting was carried out for about 10 seconds by means of a 1 ml pipet. This process was repeated twice, and then the cells were treated with the material having a negative charge to introduce a subsequent layer to the surfaces of the cells. To perform analysis with a confocal microscope, the cells were coated with a fluorescent polymer. To coat the cells with the fluorescent polymer, PLL and PLL-FITC were dissolved in α-MEM in a ratio of 9:1, and HA and HA-FITC were also dissolved in the same manner, thereby preparing a thin multilayer film in the same manner.

FIG. 1A is a schematic diagram illustrating the agitation culture process of stem cells, and FIG. 1B is a schematic diagram illustrating a process of forming the thin multilayer film on a surface of a mesenchymal stem cell (MSC). Components of the thin multilayer film are illustrated in FIG. 1C.

Experimental Example 1

Quantitative Analysis of Thin Multilayer Structure and Surface Analysis Thereof

To perform quantitative analysis of a thin multilayer film prepared according to Preparation Example 3 and to analyze a surface thereof, QCM and AFM analyses were performed.

A film prepared in a standard media was subjected to a QCM analysis. Results thereof are illustrated in FIG. 2A. It can be confirmed that, from FIG. 2A, the amounts of each of the materials adsorbed to a substrate linearly increases with increasing layer number. In the case of a general PLL/HA film, the film exponentially increased due to diffusion of a material during a film preparation process (C. Porcel et al., Langmuir, 2007, 23, 1898.). On the other hand, in the present invention, since each material was dissolved in the standard media, a film increase tendency was observed differently from those in conventional films (a thin film based on water).

It can be confirmed that, since materials (amino acids, proteins, vitamins, etc.) having electrostatic attraction among various nutrients were present in α-MEM and FBS, a substantial ion concentration increased, and diffusion and adsorption of a polymer during a thin-layer preparation process were relatively counterbalanced by coupling with ions present in a polymer chain, whereby a linearly increasing pattern was exhibited.

In addition, since large amounts of materials having a negative charge are present in the standard media, the materials are attached to the thin film in a state in which they are bound with a positively charged polymer, or are additionally attached to a film on which a positively charged polymer was adsorbed. Accordingly, a frequency rapidly decreases in an odd-numbered layer (positively charged polymer layer).

Meanwhile, a QCM result of a deionized water (DI water)-based thin film is illustrated in FIG. 2C. As a result, it can be confirmed that, when a thin film is prepared based on deionized water (DI water), PLL/HA and PLL-RGD/HA thin films exponentially increase.

In addition, it can be confirmed that a desorption phenomenon of a thin film occurs due to increased frequency change in a polymer layer having a positive charge. Such a phenomenon may be considered to occur because an attractive force between a positively charged polymer to be adsorbed and an existing thin film is greater than that between a previously uppermost polymer layer (superfacial layers) and an existing thin film, and thus, previously adsorbed polymer layers are instantaneously desorbed (H. Mjahed et al., Journal of Materials Chemistry, 2011, 21, 8416).

However, it was confirmed that a film was stably prepared due to the fact that frequency change was decreased with increasing layer number in all of the thin film preparation conditions. In addition, it was confirmed that a thin film was successfully prepared also in the case of the thin film including the RGD peptide which is a low molecular weight substance.

In general, materials, such as polymers, wherein electric charge is sufficiently present in one molecule and thus a subsequent layer can be sufficiently laminated, are mainly used in a layer-by-layer fashion. However, in the present invention, the RGD-peptide having two carboxyl groups in one molecule thereof is used, and thus, surplus ions are not present, whereby subsequent layers might not be laminated. However, in accordance with a single molecule-polymer film preparation principle suggested in the present invention, ions do not bind with each other in a correspondence of 1 to 1 when binding between counterions is induced, and ions bind with one another in a manner in which one ion is shared by multiple counterions, even in the case of a single molecule. Actually, even in the case of materials formed by ionic bonds, ions do not bind with each other in a correspondence of 1 to 1, and ions bind with one another in a manner in which one ion is shared by multiple counterions. From this fact, the thin film preparation principle can be indirectly described. In addition, when the thin film is prepared, an existing thin film is swelled and thus the RGD peptide is floated over an upper layer of the thin film, whereby surplus ions are present and thus a thin film may be prepared.

In addition, various functional groups ($NH_2$, NH, C=O bond), which may perform hydrogen bonding, are present in the RGD peptide, and thus, when a thin film is practically prepared, bonding with thin film materials may performed by hydrogen bonding as well as ionic bonding. Accordingly, although the RGD peptide is a single molecule, a thin film was successfully prepared.

Meanwhile, AFM analysis results of a thin multilayer film substrate prepared according to Preparation Example 3 are illustrated in FIG. 2B (standard media) and 2 d (DI water).

As a result, it can be confirmed that, in the case of R3, roughness is very small and thus the RGD peptide does not greatly affect the morphology of the thin multilayer film. It can be confirmed that, in the case of the standard media-based thin multilayer, dots are occasionally present in the multilayers. These dots are considered to be complexes of media ingredients and polymers. It can be confirmed that, also in the deionized water (DI water)-based thin multilayer film, dots due to polymer complexes are present in the thin film.

Experimental Example 2

Analysis of Surfaces of PS Particles Having Thin Multilayer Structure

To investigate whether the thin multilayer structure was introduced, electric charge change on the surfaces of PS particles having a thin multilayer structure prepared according to Preparation Example 2 was measured.

Results are illustrated in FIG. 3A. As illustrated in FIG. 3A, it can be confirmed that zeta potential value continuously changes according to each material layer. However, it can be confirmed that, in the case of R3, surface charge of second layer still has a positive. Basically, in a layer-by-layer fashion, an attractive force such as electrostatic attraction and hydrogen bonding is maintained by using materials having a relatively high molecular weight, and thus, a thin multilayer film is continuously prepared. However, in the case of a low molecular weight substance, the attractive force is not sufficient and the low molecular weight substance infiltrates into thin multilayer films, whereby subsequent layers tend not to be easily prepared. In addition, charge compensation is not performed in certain layers because a thin film is prepared using the standard media as a solvent and thus certain materials in the media are laminated on the surface of the film or in the interior thereof.

In addition, SEM images of PS particles to which the thin multilayer film was introduced were analyzed and are illustrated in FIG. 3B. As results, it can be confirmed that the morphologies of three particle combinations are significantly different from that of bare PS (non-coated PS particles) particles. In particular, it can be confirmed that, in the case of the H/R2 and H3 combinations, polymers are agglomerated and thus very thick and rough surfaces are exhibited. This occurs because, in the case of an α-MEM environment in which a polymer is dissolved, salts at a high concentration, vitamins, proteins, etc. are contained and thus the polymer having electric charge is agglomerated by electrical attraction with the materials in α-MEM.

Experimental Example 3

Surface Analysis of Stem Cells Having Thin Multilayer Structure

To investigate whether the thin multilayer structure was satisfactorily introduced to stem cells, stem cells having a thin multilayer structure (H3) prepared according to Preparation Example 4 were analyzed by means of a confocal microscope.

Figure 4:
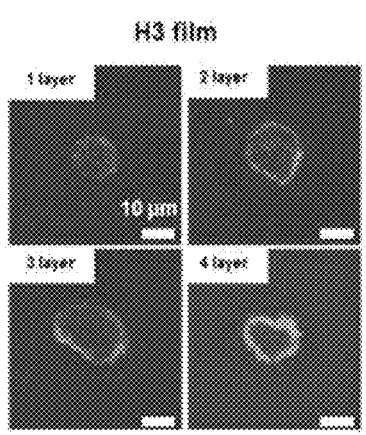
FIGS. 4A and 4B illustrate sectional views of stem cells, in which the number of layers of a thin film are different, observed by means of a confocal microscope.
Figure 4:
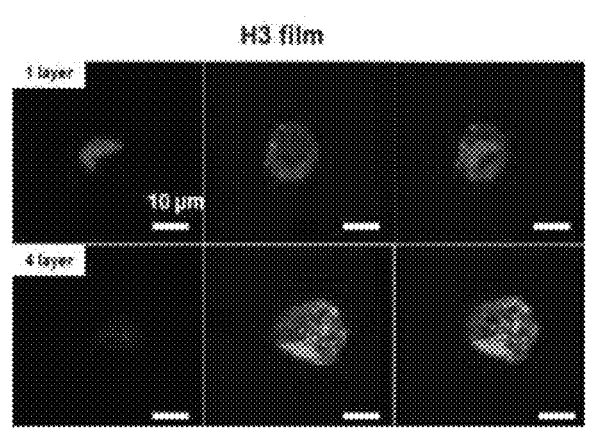
Figure 5:
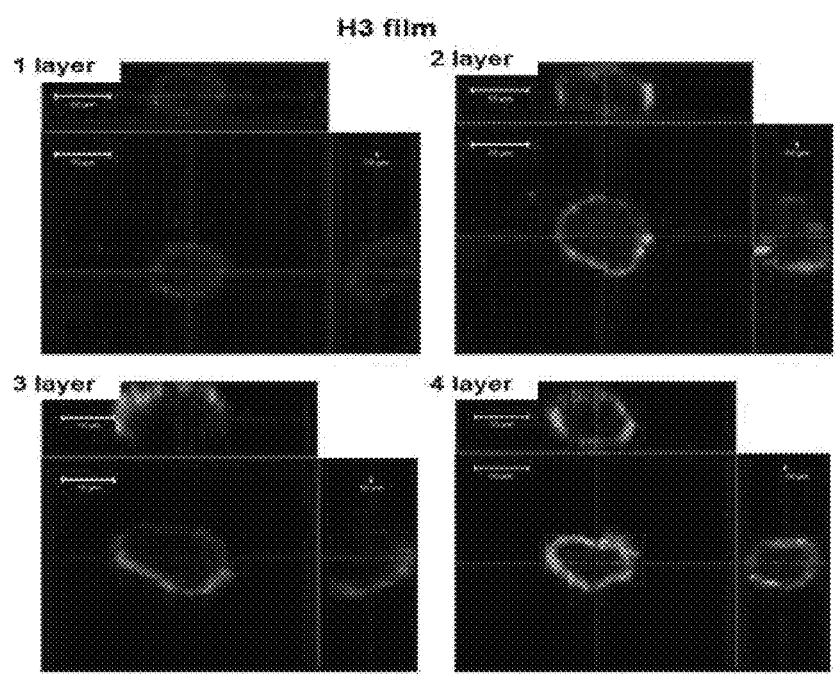
FIG. 5 illustrates images formed by dividing the images of FIG. 4A into x, y, and z axes.

Results are illustrated in FIGS. 4 and 5.

FIG. 4A illustrates sectional views of stem cells which are coated with a different number of layers. It can be confirmed that, from FIG. 4A, the thickness and intensity of FITC significantly increase with increasing number of layers. FIG. 4B illustrates three-dimensional images of cells coated with one or four layers. It can be confirmed that, from FIG. 4B, the thin multilayer film is formed with respect to the surface of a cell. As illustrated in FIG. 3B, it can be confirmed that the intensities of FITC are observed as a dot-like form on the surface of the stem cell due to agglomeration of the polymer. In addition, it can be confirmed that, from the three-dimensional images, the thin multilayer film is loosely, not densely, formed, and thus, the surface of the cell is modified without great stress.

FIG. 5 illustrates images formed by dividing the images of FIG. 4A into x, y, and z axes. It can be confirmed that most polymer layers do not infiltrate into cells and a thin multilayer film is satisfactorily formed along the surfaces of the cells.

Experimental Example 4

Investigation of Viability of Stem Cells Having Thin Multilayer Structure

Cell viability was measured to investigate whether the growth of stem cells was affected by formation of the thin multilayer film.

BMSCs not coated with the thin multilayer film and BMSCs coated with the thin multilayer film according to Preparation Example 4 were seeded at a concentration of 1×104 cells/mL onto a 100 mm petri dish, respectively. Subsequently, the seeded cells were cultured in an agitator at 65 rpm for two days (n=3). Cells were stained with trypan blue, and then the number of live cells was counted. Stirring was performed at 65 rpm, but, due to the use of a 100 mm petri dish, cells were substantially cultured at a speed of about 34 cm/s when the rpm value was calculated as a speed. The speeds of the aorta and the inferior vena cava are known to be about 40 cm/s and 15 cm/s, respectively. Therefore, the agitation culture environment of the present invention is similar to an intravascular environment.

Figure 6:
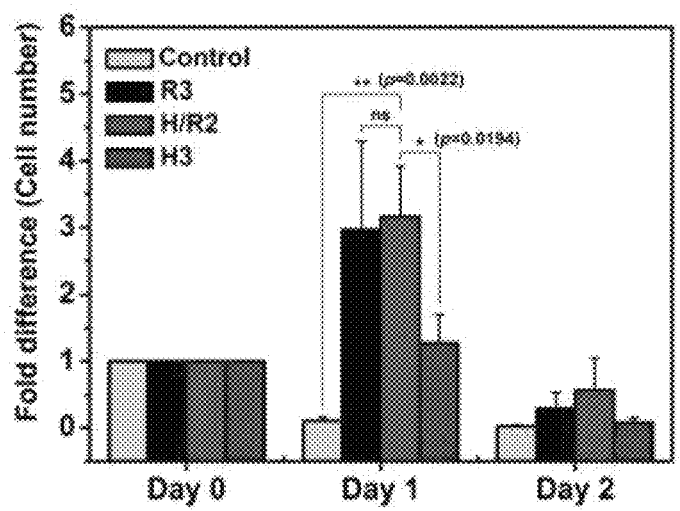
FIG. 6 illustrates viability investigation results of stem cells having a thin multilayer structure.

Results for viability are illustrated in FIG. 6. Cellular viability was investigated in an agitation culture environment. It can be confirmed that, on Day 1, the survival rate of non-coated cells (control) was greatly decreased due to high shear stress. On the other hand, it can be confirmed that, in the case of cells coated with the thin multilayer film, the number of cells increases, compared to the number of seeded cells. Such results show that cells are stably protected, due to the formed thin multilayer film, even under high external stress and thus cellular viability is improved. The results also show that the flexibility of the thin multilayer film is high enough to allow cellular proliferation. In addition, it can be confirmed that, in the case of the thin multilayer film including RGD, high survivability is exhibited, compared to the PLL/HA thin film (H3). Such a result shows that, due to the existence of RGD, RGD is bonded to integrins at the surfaces of cells, thereby much more stably protecting cells.

Meanwhile, on Day 2 after culturing, all cell types showed reduced survivability. Such a result is considered to have occurred because the cells were no longer protected due to dissociation of the thin film.

Taking the data together, it can be confirmed that, due to introduction of the thin multilayer film to surfaces of stem cells, the cells are stably protected without great affection on cellular metabolism and thus cellular functions can be satisfactorily maintained.

Experimental Example 5

Investigation of Migration Ability of Stem Cells Having Thin Multilayer Structure It was investigated whether the migration ability of stem cells having the thin multilayer film thereon was satisfactorily maintained.

BMSCs not coated with the thin multilayer film and BMSCs coated with the thin multilayer film according to Preparation Example 4 were suspended in a serum-free medium and seeded at a concentration of 5×104/200 uL onto Millicell (pore size: 12 um, diameter: 12 mm), respectively (n=4). Each of the Millicells having cells seeded thereon was inserted into each well (containing 500 uL of standard media) of a 24-well plate and culture was performed. Four hours after culturing, the Millicells were treated with 4% paraformaldehyde for 20 minutes and washed with PBS, thereby fixing the cells. To investigate the cells, the cells were stained with methyl violet. Non-migrated cells were wiped with gauze and then the number of migrated cells was calculated by means of a microscope. The number of migrated cells was statistically analyzed through the Image J program.

Figure 7:
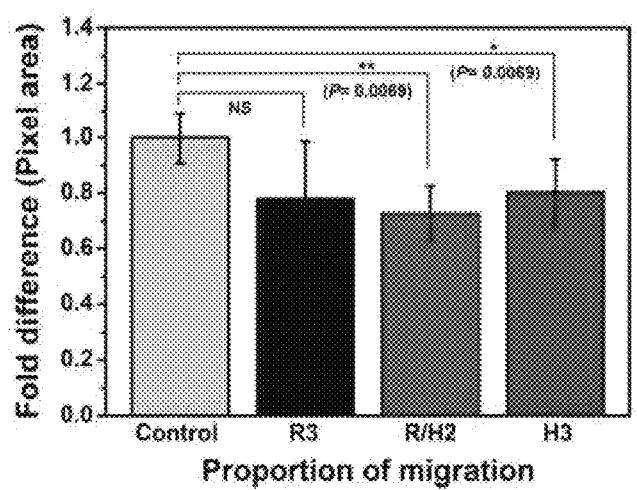
FIG. 7 illustrates migration ability investigation results of stem cells having a thin multilayer structure.

As results, it can be confirmed that, as illustrated in FIG. 7, the migration ability of the stem cells having the thin multilayer film thereon is about 80%, when the migration ability of the non-coated control is 100%. Such a result shows that the formed thin multilayer film does not greatly affect cell migration.

Experimental Example 6

Investigation of Differentiation of Stem Cells Having Thin Multilayer Structure into Adipocytes It was investigated whether stem cells having the thin multilayer structure prepared according to Preparation Example 4 were differentiated into adipocytes. After forming the thin film on cells, the cells were seeded onto a 6-well plate, and then cultured for three weeks such that they were spontaneously differentiated into adipocytes (spontaneous adipogensis). After three weeks, the cells were stained with Oil red O that can bind with fat in adipocytes. First, a medium was removed and then the cells were fixed with 10% formalin. Subsequently, after treatment with Oil red O, the cells were allowed to sit for one hour at room temperature. Treatment with 60% isopropanol was performed to dissolve dye adhering to sites except for fat, and then treatment with Harris hematoxylin was performed to stain nuclei. Finally, treatment with 1% acetic acid was performed, followed by washing. The area of each of the stained wells was calculated.

Figure 8:
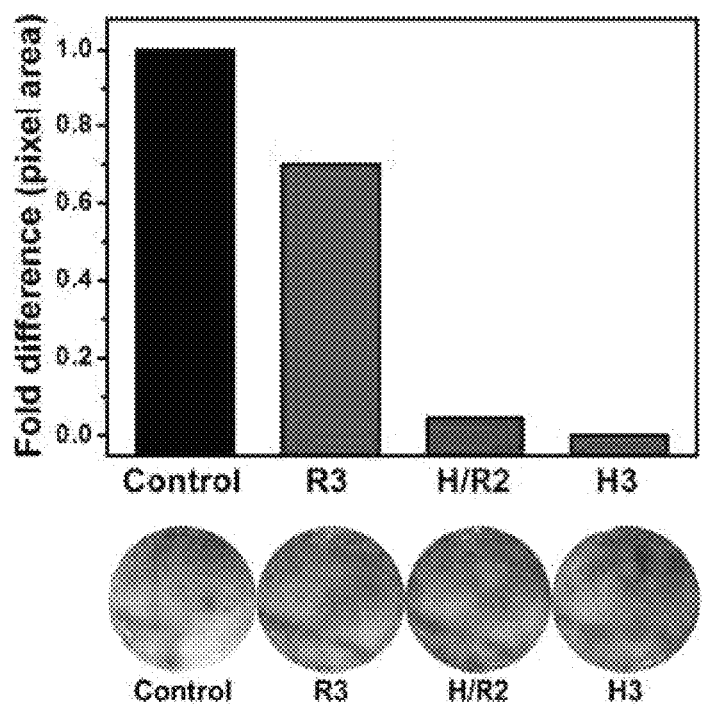
FIG. 8 illustrates the degree of differentiation into adipocytes of stem cells having a thin multilayer structure.

The stem cells having the thin multilayer structure were cultured to induce spontaneously differentiation into adipocytes (spontaneous adipogensis). As results, it can be confirmed that, as illustrated in FIG. 8, the degree of differentiation into adipocytes depends upon the laminated thin film. In particular, differentiation into adipocytes is easily performed with an increasing amount of the RGD peptide laminated in the thin film and, on the other hand, in the case of the thin multilayer film made of HA, the degree of differentiation is reduced. Such a result may be considered to be caused by the functional groups included in the thin film material. Actually, it has been reported that, when stem cells were cultured with a polymer, such as HA, having many carboxyl groups, the stem cells were differentiated into cartilage cells (Danielle S. W. Benoit et al., Nature Materials, 2008, 7, 816.). In addition it has been reported that, when stem cells were cultured with the RGD peptide, the stem cells were actively differentiated into adipocytes (S.-W. Kang et al., Macromolecular Bioscience, 2011, 11, 673.).

Such results suggest that stem cells may be differentiated into various cells by controlling the composition of the thin film and, accordingly, a technology of differentiating stem cells into target tissues may be developed.

Experimental Example 7

Investigation of Viability of Stem Cells Having Thin Multilayer Structure in Blood Vessel Rat mesenchymal stem cells from a green fluorescence protein (GFP) positive rat were obtained through primary culture. An H/R2 film was formed on surfaces of rat GFP (+) MSCs, as in Preparation Example 4.

Subsequently, the stem cells having the thin multilayer structure (H/R2) and cells with no thin multilayer film formed thereon were injected into the tail veins of nude mice, respectively (5×105 cells/mouse, n=5) (cells were dispersed in saline before use).

At each time point (6 h, 24 h, 48 h, 72 h), the whole blood was collected from the heart of each of the nude mice.

Only mononuclear cells (MSCs were also included therein) were isolated and FACS was performed to investigate whether GFP (+) MSCs were present in the isolated cells.

Results are illustrated in FIGS. 9A through 9C. In particular, it can be confirmed that the stem cells having the thin multilayer film are alive in a larger number up to 72 hours. Accordingly, it can be confirmed that the stem cells having the thin multilayer structure are more stably present in the blood vessel and also secure under bloodstream stress, other clearance stress, etc.

FIG. 9A illustrates FACS results of a positive control (GFP (+) cells) and a negative control (general cells). It can be confirmed that the positive control exhibits very high fluorescence intensity (x axis: GFP fluorescence intensity, y axis: cell count number)

FIG. 9B illustrates FACS results of a control (cells not having the thin multilayer film) and the cells having the H/R2 film at each time point. In the case of the cells having the thin film, high fluorescence intensity is observed at all time points. That is, it can be confirmed that GFP MSCs having the thin film are present in a higher proportion in the blood.

FIG. 9C illustrates a GFP (+) cell percentage at each time point based on FIGS. 9A and 9B. It can be confirmed that, from FIG. 9C, the cells coated with the thin multilayer film are present in a higher proportion in the blood at all time points.

Experimental Example 8

Investigation of Wound Healing Effect of Stem Cells Having Thin Multilayer Structure Rat mesenchymal stem cells from a GFP (green fluorescence protein) positive rat were obtained through primary culture. The H/R2 film was formed on surfaces of the rat GFP (+) MSCs as in Preparation Example 4.

Subsequently, the stem cells having the thin multilayer structure (H/R2) and cells not having the thin multilayer film were injected into the tail veins of nude mice, respectively (1×106 cells/mouse, n=5) (cells were dispersed in saline before use)

At 12 hours after injection, the thigh muscles of the mice were damaged such that MSCs were able to gather at the damaged sites. On day 2 after injection, the muscles were photographed (FIG. 10A).

In addition, the damaged muscles were photographed by means of a two photon microscope to observe GFP (+) cells. It was observed how many MSCs gathered at the muscles. As a result, it was confirmed that the stem cells having the thin multilayer structure gathered in a higher proportion at the wound area.

Mesenchymal stem cells have a characteristic in which they gather at a wound area and treat the wound. It can be confirmed that the stem cells having the thin multilayer structure present in a higher proportion in the bloodstream more rapidly gather in a higher proportion at the wound area.

FIG. 10A illustrates injured muscles and non-injured muscles. It can be observed that the injured muscles are red and swollen.

FIG. 10B illustrates images photographed with a two photon microscope. By bright-field DIC imaging, muscle shapes were satisfactorily observed. It can be confirmed that, by FITC imaging, GFP positive cells having the thin multilayer structure are present in a higher proportion at the wound area.

As described above, the present invention can provide stem cells with a thin multilayer structure having improved stability and controlled multifunctionality. In addition, since the method of preparing the stem cells having the thin multilayer structure according to the present invention is very simple, the stem cells having the thin multilayer structure can be produced at low cost and high efficiency. Therefore, the stem cells having the thin multilayer structure prepared according to the present invention are very useful as a stem cell therapy agent for treating various diseases.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An intravenous injection composition having a thin multilayer structure,
    wherein the composition comprises a stem cell; a cationic material layer formed on the stem cell; and an anionic material layer formed on the cationic material layer;
    wherein the cationic material is poly-L-lysine the anionic material is hyaluronic acid or an RGD peptide; and
    wherein the cationic material layer and the anionic material layer are alternately laminated two more times; and at least one layer of the anionic material comprises an RGD peptide.

2. A method of healing wound, the method comprising intravenously administering the composition having the thin multilayer structure according to claim 1 to the wound in a therapeutically effective amount.

3. A method of preparing an intravenous injection composition having a thin multilayer structure, the method comprising:
    a step of laminating a cationic material on a stem cell in a layer-by-layer fashion to form the cationic material layer on the stem cell;
    a step of laminating an anionic material on the cationic material layer in a layer-by-layer fashion to form the anionic material layer on the cationic material layer; and
    a step of alternately forming the cationic material layer and the anionic material layer two more times,
    wherein the cationic material is poly-L-lysine the anionic material is hyaluronic acid or an RGD peptide; and
    at least one layer of the anionic material layer comprises an RGD peptide.

* * * * *